United States Patent [19]
Heller et al.

[11] Patent Number: 6,135,990
[45] Date of Patent: Oct. 24, 2000

[54] ELECTROPORATION DEVICE AND METHOD

[75] Inventors: Richard Heller, Temple Terrace; Richard Gilbert; Mark Jaroszeski, both of Tampa, all of Fla.

[73] Assignee: University of South Florida, Tampa, Fla.

[21] Appl. No.: 09/213,210

[22] Filed: Dec. 17, 1998

Related U.S. Application Data

[60] Provisional application No. 60/069,876, Dec. 17, 1997.

[51] Int. Cl.⁷ .................................................. A61M 31/00
[52] U.S. Cl. ......................... 604/500; 604/20; 435/173.6
[58] Field of Search ............................... 604/19, 20, 500, 604/501; 435/173.4, 173.5, 173.6, 283.1, 285.2

[56] References Cited

U.S. PATENT DOCUMENTS

| | | | |
|---|---|---|---|
| 5,869,326 | 2/1999 | Hofmann | 435/285.2 |
| 5,873,849 | 2/1999 | Bernard | 604/20 |
| 5,941,845 | 8/1999 | Tu et al. | 604/53 |
| 5,944,715 | 8/1999 | Goble et al. | 606/41 |
| 5,964,726 | 10/1999 | Korenstein et al. | 604/20 |

*Primary Examiner*—Glenn K. Dawson
*Assistant Examiner*—Michael J. Hayes
*Attorney, Agent, or Firm*—Allen,Dyer,Doppelt, Milbrath & Gilchrist,P.A.

[57] ABSTRACT

A device for manipulating a molecule in vivo relative to a target tissue in three dimensions includes a support and at least one member affixed to and extending away from the support. The member has at least two discrete and separately activatable electrodes. The electrodes are configured to establish a first electromagnetic field between selected electrodes sufficient to manipulate a molecule relative to a target tissue. The electrodes are further configured to establish a second, typically higher-level, electromagnetic field sufficient to cause transient permeability of a cell membrane within the target tissue. A third electromagnetic field may also be applied to cause further translation of the molecule into an electropermeabilized cell and/or manipulated with respect to the tissue. Thus three-dimensional manipulation of the molecule relative to the target tissue is effected to optimize a desired positioning thereof, such as entry into a cell.

28 Claims, 6 Drawing Sheets

ELECTROPORATION DEVICE AND METHOD

CROSS-REFERENCE TO RELATED APPLICATION

This application claims priority from previously filed provisional application, "Methods and Apparatus for Three Dimensional Distribution of Molecules within Tissues and Cells in Vivo," Ser. No. 60/069,876, filed Dec. 17, 1997.

BACKGROUND OF THE INVENTION

1. Field of the Invention

The present invention relates to methods and apparatus for delivering molecules into a target cell, and, more particularly, to such methods and apparatus for achieving such delivery through electroporation and electromigration.

2. Description of Related Art

The effect of electromagnetic fields on cell membranes has been studied since the 1960s. Early research focused on describing observations that an applied electric field can reversibly break down cell membranes in vitro. Throughout the 1970s the topic was more common in the literature and continued to focus on describing the phenomenon that resulted from brief exposure to intense electric fields as well as the entry of exogenous molecules to the cell interior as a result of membrane breakdown. Applications began to emerge along with a better understanding of reversible membrane breakdown in the 1980s.

Prior research led to the current understanding that exposure of cells to intense electric fields for brief periods of time temporarily destabilized membranes. This effect has been described as a dielectric breakdown due to an induced transmembrane potential, and was termed "electroporation," or "electropermeabilization," a because it was observed that molecules that do not normally pass through the membrane gain intracellular access after the cells were treated with electric fields. The porated state was noted to be temporary. Typically, cells remain in a destabilized state on the order of minutes after electrical treatment ceases.

The physical nature of electroporation makes it universally applicable. A variety of procedures utilize this type of treatment, which gives temporary access to the cytosol. These include production on monoclonal antibodies, cell-cell fusion, cell-tissue fusion, insertion of membrane proteins, and genetic transformation. In addition, dyes and fluorescent molecules have been used to investigate the phenomenon of electroporation. A notable example of loading molecules into cells in vivo is electrochemotherapy. The procedure utilizes a drug combined with electric pulses as a means for loading tumor cells with an anticancer drug, and has been performed in a number of animal models and in clinical trials by the present inventors. Also, plasmid DNA has been loaded into rat liver cells in vivo (Heller et al., FEBS Lett. 389, 225–28).

Protocols for the use of electroporation to load cells in vitro typically use a suspension of single cells or cells that are attached in a planar manner to a growth surface. In vivo electroporation is more complex because tissues are involved. Tissues are composed of individual cells that collectively make up a three-dimensional structure. In either case, the effects on the cell are the same. FIG. 1 illustrates details of the electrical treatment procedure. Electrodes and electrode arrays for delivering electrical waveforms for therepeutic benefit, including inducing electroporation, have been described by Bernard (WO 98/47562).

The loading of molecules by electroporation in vitro as well as in vivo is typically carried out by first exposing the cells or tissue of interest to a drug or other molecule (FIG. 2). The cells or tissue are then exposed to electric fields by administering one or more direct current pulses. Electrical treatment is conducted in a manner that results in a temporary membrane destabilization with minimal cytotoxicity. The intensity of electrical treatment is typically described by the magnitude of the applied electric field. This field is defined as the voltage applied to the electrodes divided by the distance between the electrodes. Electric field strengths ranging from 1000 to 5000 V/cm have been used for delivering molecules in vivo and are also specific to the cells or tissue under investigation. Pulses are usually rectangular in shape; however, exponentially decaying pulses have also been used. The duration of each pulse is called pulse width. Molecule loading has been performed with pulse widths ranging from microseconds ($\mu$s) to milliseconds (ms). The number of pulses delivered has ranged from one to eight. Typically, multiple pulses are utilized during electrical treatment.

For molecules to be delivered to the cell interior by electroporation, it is important that the molecule of interest be near the exterior of the cell membrane when in the cell is in a permeabilized state. It is also important to have molecules near substantially all cells within a treated tissue volume in order to provide efficient delivery to substantially all cells within the treatment volume.

Currently, molecules are injected systemically, via methods well known to those of skill in the art, or directly into the treatment site. No attempt is made to produce a specific distribution. These methods do not ensure that the distribution of molecules is sufficient to provide effective delivery to substantially all the cells.

Electropermeabilization of tumor cell membranes in vivo has been reported (Rols et al., *Nature Biotechnology* 16, 173, 1998) using applied electric pulses from surface electrodes in contact with the skin. A protein can be transferred into or and expressed by the cells by incorporating either the protein or a plasmid carrying a reporter gene. The efficiencies of transfer for the protein and plasmid were, respectively, 20 and 4%.

A first type of electrode known in the art comprises parallel-plate electrodes placed on opposite sides of the tumor. Other electrodes known in the art at the present time comprise needles that are inserted into or around the tissue of interest. Electric fields are applied in only two dimensions of the three-dimensional tissue matrix. This limits the area of each cell that can be electroporated (FIG. 1), which reduces delivery efficiency.

A two-dimensional array of needles has also been disclosed (Gilbert et al., *Biochim. Biophys. Acta* 1334, 9, 1997; U.S. Pat. No. 5,702,359) in which circularly disposed pairs of needles surround a target tissue. Pulses of opposite polarity are applied across each pair of needles in a predetermined sequence, which has been shown to improve tumor regression in a mouse melanoma study.

Electrodes and methods known in the art do not provide molecule movement during the preelectroporation period to enhance molecular distribution nor in the postelectroporation time period, when the cells are in a state of increased membrane permeability. The movement of molecules within the tissue is believed to effect an increase in the delivered quantity of molecules by enhancing movement into the cells.

SUMMARY OF THE INVENTION

It is therefore an object of the present invention to provide an improved device and method for manipulating molecules adjacent and/or within a target tissue site.

It is an additional object to provide such a device and method for manipulating molecules in three-dimensional space such as a tissue volume element.

It is a further object to provide such a device and method that can provide a desired electromagnetic field distribution adjacent and/or within a target tissue.

It is another object to provide such a device and method that can be configured to activate a multicomponent labile system at a desired site.

It is yet an additional object to provide a system for effecting tumor reduction.

It is yet a further object to provide a system for effecting in vivo gene transfer to cells via electroporation.

These objects and others are attained by the present invention, a device for manipulating a molecule in vivo relative to a target tissue in three dimensions. The device comprises a support and at least one member affixed to and extending away from the support. The member has at least two discrete electrodes, each electrode in independent circuit communication with a respective portion of a source of electrical energy and therefore being differentially activatable.

The discrete electrodes are configured to establish a first electromagnetic field in vivo between selected electrodes sufficient to manipulate a molecule translationally relative to a target tissue. The electrodes are further configured to establish a second electromagnetic field sufficient to cause transient permeability of a cell membrane within the target tissue. In a particular embodiment the electrodes are also configured to establish a third electromagnetic field sufficient to manipulate a molecule translationally following the second field to continue it enhancing molecular distribution and/or uptake at cells. Typically the first and the third field levels will be lower than that of the second, although this is not intended as a limitation.

In an alternate embodiment, a system includes at least two members extending from a support. A first member includes at least one electrode as described above; a second member includes at least two electrodes. Such an arrangement permits triangulation between the independently activatable electrodes.

In a particular embodiment the electrodes are activatable in a predetermined sequence, which may include sequential or simultaneous activation of any or all of the electrodes.

The device can be used, for example, with alternating current, direct current, pulsed alternating current, pulsed direct current, high- and low-voltage alternating current with variable frequency and amplitude, variable direct current waveforms, variable alternating current signals biased with variable direct current waveforms, and variable alternating current signals biased with constant direct current.

Several embodiments of the methods of the present invention include the use of a device as described above to enhance the delivery of a molecule such as a bioactive molecule, nucleic acid, amino acid, polypeptide, protein, antibody, glycoprotein, enzyme, oligonucleotide, plasmid DNA, chromosome, or drug, although this list is not intended to be exhaustive or limiting. In a related embodiment the device may be used to cause the electromigration of at least two components of a multicomponent reactive system into apposition to permit a reaction to occur at a desired target tissue site. The target tissue may comprise a tumor, and organ, or wound site.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 2 (prior art) The process of delivering molecules by electroporation.

DETAILED DESCRIPTION OF THE PREFERRED EMBODIMENTS

Figure 1:
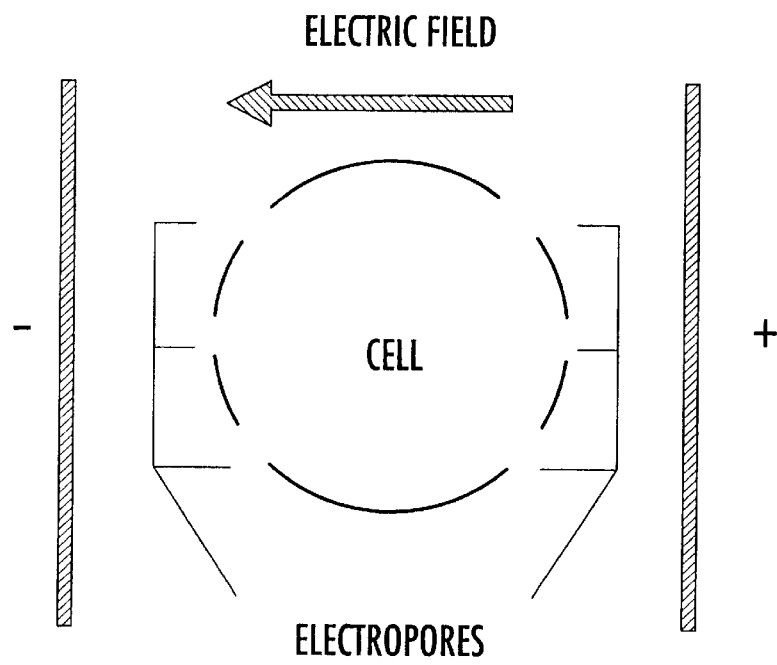
FIG. 1 (prior art) Conceptual two-dimensional depiction of electroporation of a cell subjected to an electromagnetic field. Regions of membrane breakdown, depicted as pores, are formed at the ends of cells facing the electrodes. Electromagnetic field exposure is achieved by applying a potential between electrodes − and +.
Figure 2A:
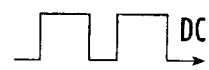
FIG. 2A. Cells in vitro or in vivo are exposed to the molecule of interest.
Figure 2A:
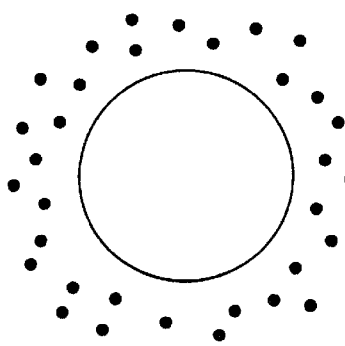
Figure 2B:
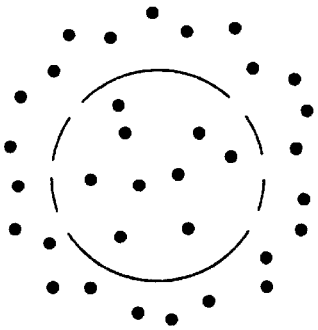
FIG. 2B. Direct current pulses are administered to the cells to cause a temporary membrane destabilization that allows the molecules to more freely enter the cell interior.
Figure 2C:
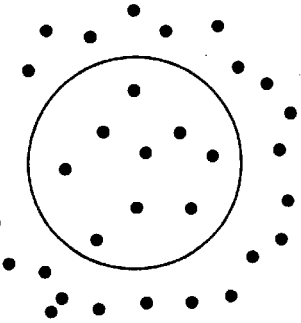
FIG. 2C. Cells return to their normal state after pulsation, leaving the molecule within the cells.
Figure 3:
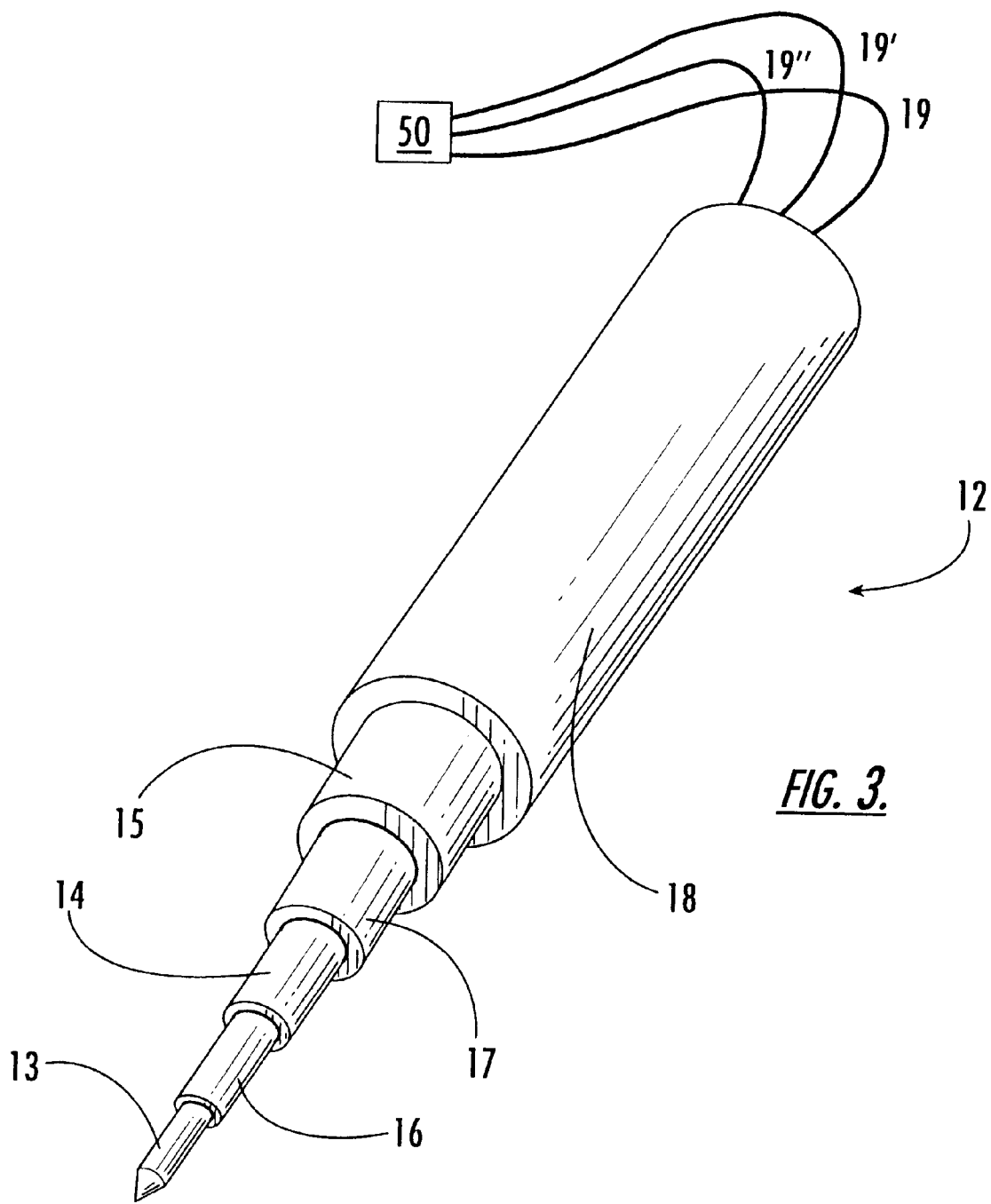
FIG. 3 A first embodiment of one electrode-bearing member of a molecule manipulator, including radially disposed coaxial electrodes spaced apart by nonconductive material.
Figure 4:
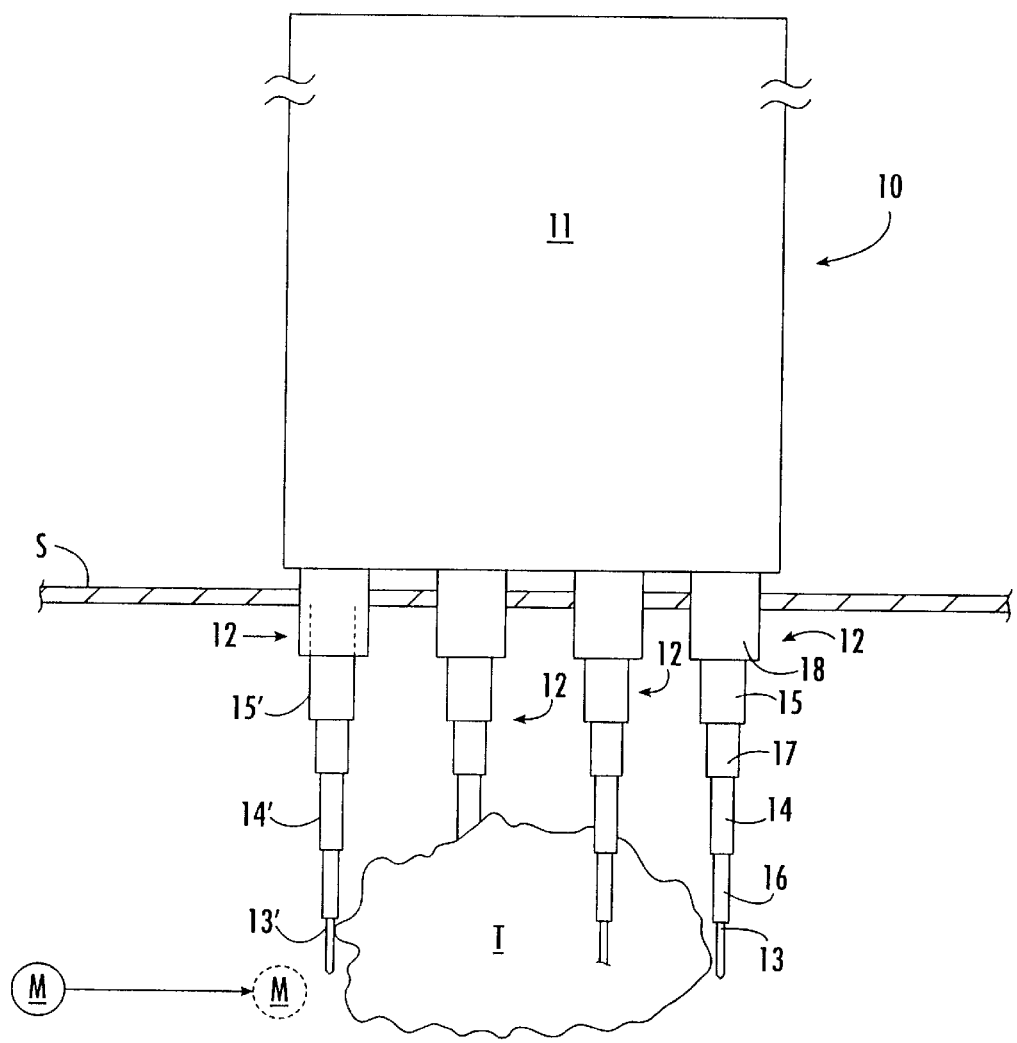
FIG. 4 A molecule manipulator including a support and plural members as in FIG. 3.
Figure 5:
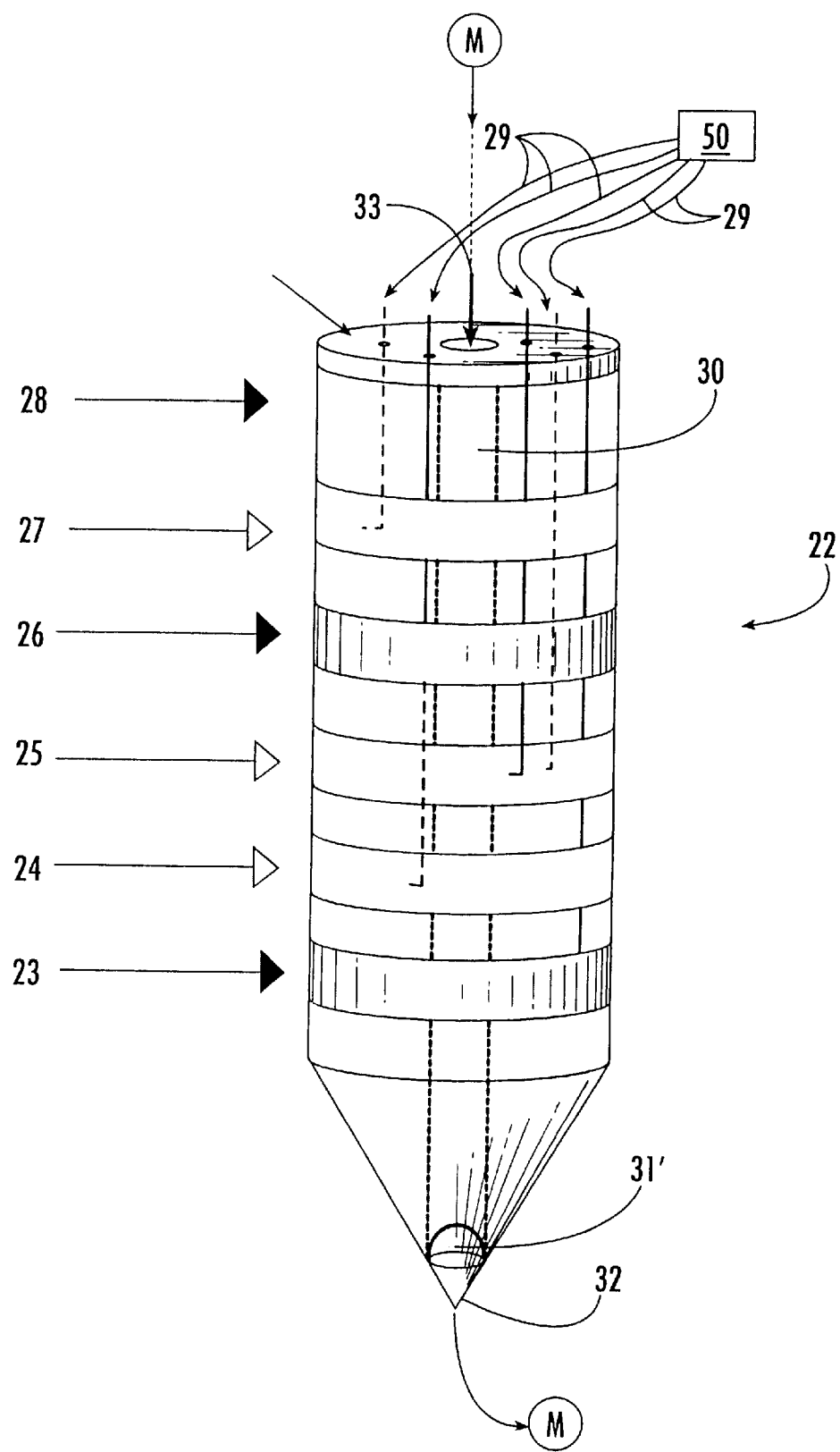
FIG. 5 A second embodiment of one electrode-bearing member of a molecule manipulator, including circumferential bands of electrodes disposed along a generally cylindrical electrode.

A description of the preferred embodiments of the present invention will now be presented with reference to FIGS. 3–7.

A first embodiment of a device 10 for manipulating a molecule M in vivo relative to a target tissue T (FIGS. 3 and 4) comprises a support 11 that is adapted to reside outside the site of the target tissue T, here shown as atop the skin S, although this is not intended as a limitation. At least one member 12, here shown as four members 12, are affixed to and extend away from the support 11. The members 12 are preferably disposed about the support 11 in spaced relation from each other and are configured to surround a periphery of and/or penetrate into at least a portion of the target tissue T, with at least a lower portion of the members 12 penetrating the skin S (or other organ or tissue) to reach the target tissue T. Here the target tissue is T represented as a tumor, although this is not intended to be a limitation.

Each member 12 has at least two discrete electrodes disposed in axially spaced-apart relation from each other, here shown as three electrode portions 13,14,15. Each electrode 13–15 is in circuit communication with a respective portion of a source 50 of electrical energy. The term "in circuit communication" as used herein is used to describe (1)

devices that are directly or indirectly electrically connected with each other; (2) devices having other devices or combinations of devices (e.g., breakers, relays, buffers, drivers, transmitters, receivers, and decoders) between them; (3) devices in optical communication with each other (via, e.g., an optoisolator or fiber optic link); (4) devices in electromagnetic communication with each other (via, e.g., radio frequency transmitter and receiver pair); (5) devices connected by and through other structures allowing them to communicate with each other; and (6) any combination of any of the above.

In a preferred embodiment this source comprises a pulse generator such as is known in the art (e.g.,a PA-2000 or PA-4000, both from Cyto Pulse Sciences, Inc., Columbia, Md.; a T820, BTX, Inc., San Diego, Calif.) and adapted to deliver pulses of a predetermined shape, voltage, duration, and separation. In particular, the source 50 should be adapted to deliver voltage to each electrode 13–15 for establishing a lower-level and a higher-level electromagnetic field in vivo between selected electrodes. Selective control of the application of electrical signals between the individual electrodes can be accomplished in different ways, e.g., via the PA-201 Programmable Pulse Switch in combination with the PA-4000 generator (both from Cyto Pulse Sciences, Inc., Columbia, Md.) or it can be done manually, mechanically, or electrically.

The lower-level field is for manipulating (e.g., causing the electromigration of) the molecule M in three-dimensional fashion relative to the target tissue T, here shown as a mass. The higher-level field is for causing transient permeability of a cell membrane within the target tissue T. Such a permeability is useful for permitting the molecule M to enter the interior of the cell (see FIGS. 1 and 2). A lower-level field can also be applied following the application of a higher-level field to enhance molecule distribution within the target tissue and/or cause movement of the molecule(s) into the cell interior of the permeabilized cell by electroporation.

In the first embodiment, the member 12 comprises an elongated and pointed core electrode 13 that is made of a conductive material. A nonconductive insulator sleeve 16 is positioned in surrounding relation to a portion of the core electrode 13, with a bottom portion of the core electrode 13 protruding and thus exposed.

A first outer electrode 14 is positioned in surrounding relation to a portion of the sleeve 16, with a bottom portion of the sleeve 16 protruding therefrom and thus exposed.

A second sleeve 17 is positioned in surrounding relation to a portion of the first outer electrode 14, with a bottom portion of the second electrode 14 protruding therefrom and thus exposed.

A second outer electrode 15 is positioned in surrounding relation to a portion of the second sleeve 17, with a bottom portion of the second sleeve 17 protruding therefrom and thus exposed.

A third sleeve 18 is positioned in surrounding relation to a portion of the second outer electrode 15, with a bottom portion of the second outer electrode 15 protruding therefrom and thus exposed.

In a prototype embodiment, which is not intended as a limitation, the device 10 comprises a stainless steel 30-gauge needle as the core electrode 13 placed in the hollow space of a 25-gauge hypodermic tubing as the first outer electrode 14 with a layer of nonconductive insulation between the electrodes 13,14 as the first sleeve 16. A layer of insulation is placed over the first outer electrode 14 to serve as second sleeve 17, and a section of 23-gauge tubing, serving as second outer electrode 15, is placed over the second sleeve 17. Insulation placed over the second outer electrode 15 serves as third sleeve 18. The bottom portions of each of these elements are exposed to form a series of conductive bands 13–15 separated by nonconductive regions 16–18.

This arrangement provides three electrodes exposed to the exterior with an insulator between each adjacent pair of electrodes. It can be appreciated by one of skill in the art that any number of electrodes and insulators could be successively configured in overlapping fashion to produce a multielectrode member tailored to a particular application based upon such considerations as, for example, the size of the target tissue and the space available.

Each electrode 13–15 has an independent lead 19, 19', 19", respectively, affixed to its top end to provide the circuit communication with the pulse generator.

In use the members 12 are typically arranged in opposing spaced-apart pairs, so that at least one electrode on each of a pair of members 12 can be adapted to provide at least one pair of opposite-polarity voltages approximately simultaneously. Further, it may be desired to selectively apply electrical potentials to each electrode pair in a predetermined pattern. Such a means for imposing a preselected pattern may include, for example, a software program for driving a pulse generator to deliver signals to each selected electrode in the preselected pattern.

It can be seen that three-dimensional manipulation can be effected by activating opposing pairs of electrodes at different axial levels to induce molecular movement and/or electropermeabilization along a desired pathway. For example, activating the pair 13–13' would induce movement generally in a plane normal to the member 12, whereas activating the pair 13–15' would induce movement at an angle relative to the plane. These presupposed movements are, of course, subject to other conditions within and surrounding the tissue, and are only to be construed as relative and indicative of possible general directionalities achievable by the devices of the present invention.

Figure 6:
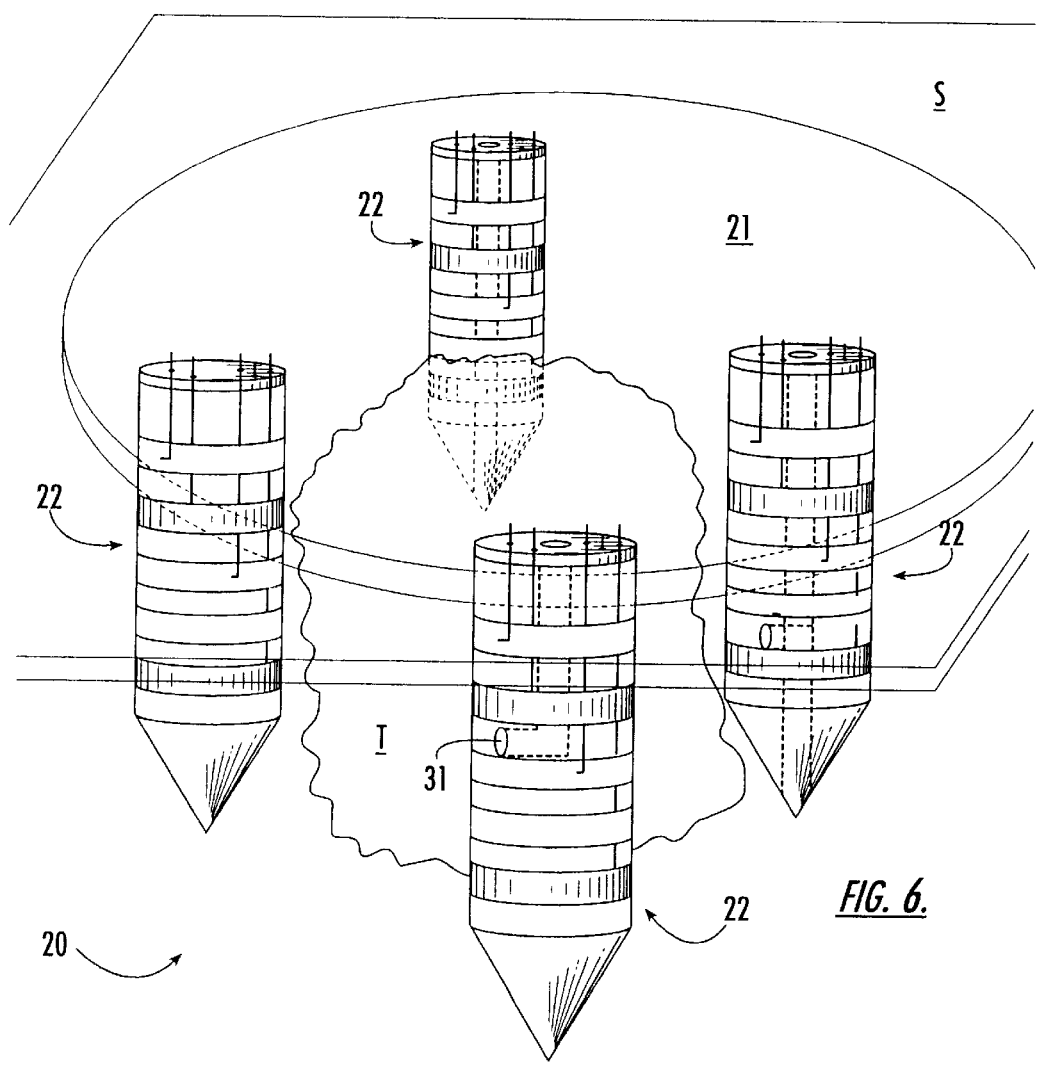
FIG. 6 A molecule manipulator including a support and plural members as in FIG. 5.
Figure 7:
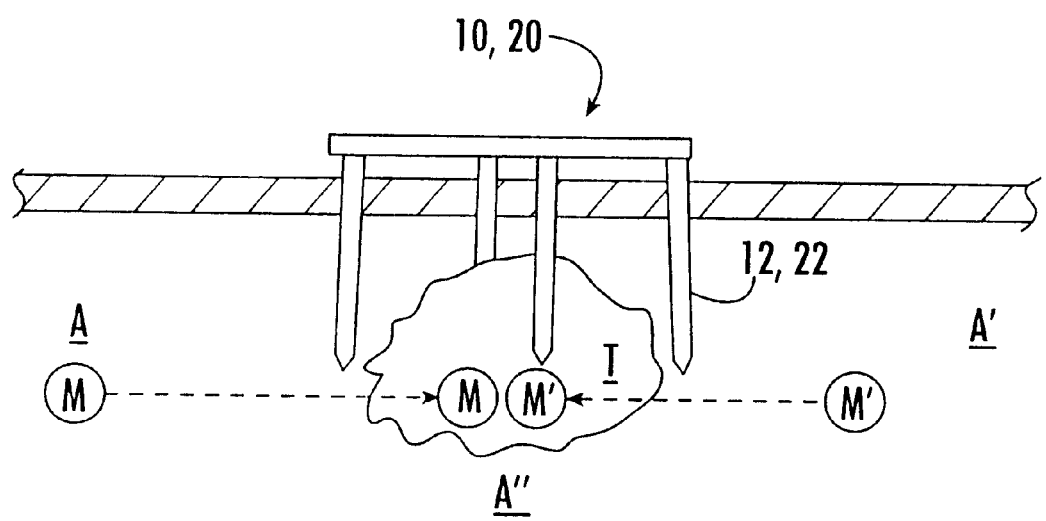
FIG. 7 The use of a molecule manipulator to bring components of a multicomponent reactive system into apposition at a target tissue site.

A second embodiment of a device 20 for manipulating a molecule M in vivo relative to a target tissue T (FIGS. 5 and 6) comprises a support 21 and at least one member 22, here shown as four members 22, affixed to and extending away from the support 21. The members 22 are preferably disposed about the support 21 in spaced relation from each other and are configured to surround a periphery of and/or penetrate into at least a portion of the target tissue T. In FIG. 6 the target tissue is T represented as a tumor, although this is not intended to be a limitation.

Each member 22 has at least two discrete electrodes, here shown as five electrodes 23–27 configured as circumferential rings disposed about a generally cylindrical nonconducting core post 28. As above, each electrode 23–27 is in independent circuit communication with a respective portion of a source 50 of electrical energy. Such independent circuit communication may be formed, for example, by respective insulated leads 29 extending through the core 28 from the top end to each ring electrode 23–27.

Additionally, the core 28 may have a lumen 30 therein extending from a top opening 33 for dispensing a molecule M to a tissue through a portal 31. The portal 31 in one embodiment may be adjacent an electrode or may 31' be at the core's tip 32, which in a particular embodiment may be pointed.

Several embodiments of methods of the present invention will now be disclosed. These methods will be illustrated with the device 10 described above, although this is not intended as a limitation, since either device 10 or 20 could be used therein, or other equivalents appreciated by one of skill in the art.

A first embodiment comprises a method for achieving an improved distribution and delivery of a desired molecule M into a target tissue T. This method comprises the steps of inserting at least one elongated member 12 into a body tissue generally adjacent and/or within a target tissue T. Such an insertion may be aided by any of the visualization techniques known in the art, such as computed tomography, ultrasound, x-radiography, although these are not intended as limitations. A substance that includes the desired molecule M, such as a solution thereof, is introduced into the body into an area near the target tissue T, either before or after the insertion of the device 10. A particular introduction method comprises delivering the substance through a lumen 30 and portal 31 as in the embodiment of FIGS. 5 and 6. Any other method of introduction such as known to one of skill in thevart may also be employed.

A first electrical potential is established between a pair of electrodes 13–15' that is sufficient to cause a redistribution and electromigration of the desired molecule M toward the target tissue T. Then subsequently a second electrical potential is established between a pair of electrodes, which may or may not be the same electrode pair as previously activated. The second potential has a sufficiently high electrical potential to cause electroporation in the target tissue T to enhancing a movement of the desired molecule M into a cell. An additional, third, low-level field after electroporation induction can be applied to further enhance molecular movement into cells and/or redistribution. Exemplary pulse magnitude and duration ranges include, but are not intended to be limited to, 1–10,000 volts/cm for a duration in the nanosecond to second range. A particular embodiment comprises a pulse or plurality of pulses in a range of 1–500 V/cm for a duration in the millisecond range for the first and the third potentials and a pulse or plurality of pulses in a range of 750–1500 V/cm in the microsecond range for the second potential. Naturally these values are not intended to be limiting, and one of skill in the art will appreciate that, for example, shorter pulses of higher magnitude or longer pulses of lower magnitude may be employed as required to achieve the desired effect.

A second method is for delivering a bioactive molecule to a subcutaneous target tissue T. This method comprises the steps of, as above, introducing a substance containing the bioactive molecule M systemically or into a subcutaneous area adjacent the target tissue T. A device such as device 10 is inserted into a body tissue generally adjacent a target tissue T, and electrode pairs are again activated at a low and high and again low level to achieve, respectively, an electromigration of the bioactive molecule M adjacent and within the target tissue T, an electroporation of a cell membrane within the target tissue T sufficient to permit entry of the bioactive molecule M into the cell interior, and additional electromigration within the target tissue.

A third method (FIG. 7) is for bringing two molecules M,M' into apposition at a desired target tissue site T for permitting a reaction therebetween, as in multicomponent reactive system, or a cell "bomb." This method comprises the steps of introducing a substance containing a first molecule M into a first area A adjacent and/or within the target tissue site T and introducing a substance containing a second molecule M' into a second area A' adjacent and/or within the target tissue site T.

Next an electromigration of the first M and the second molecule M' is caused to a third area A" that is adjacent and/or within the target tissue site T. The third area A" may actually comprise the first A or the second area A', or another area distinct therefrom.

Next the first M and the second M' molecule are permitted to react at the third area A".

It may be appreciated by one skilled in the art that additional embodiments may be contemplated, including different electrode configurations adapted to provide high- and low-level fields for causing electromigration and electroporation. In this application, a device being "configured" to produce an electromagnetic field in vivo means that (i) the portion of the device that comes in contact with body tissue or fluid is made of biocompatible materials, (ii) the electrodes are capable of carrying the current required for electroporation and/or electromigration of living cells in vivo in an electrolyte which may include the tissue being treated, interstitial fluid, injected material at the treatment site, material applied to the target tissue, and combinations of the foregoing, and (iii) the material between the electrodes on each support member, which may be the same material as the support member, should have a sufficient dielectric constant so that it does not break down as a result of nearby electrodes being of opposite polarity during electrical treatment. Moreover, it will be apparent to those skilled in the art that where an electrode or system is configured to perform both electromigration and electroporation, such an electrode or system may be used to perform either or both functions.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for manipulating a molecule in vivo relative to a target tissue comprising:

a support and at least two spaced-apart members affixed to and extending away from the support, the members each having at least two discrete, individually activatable electrodes disposed in axially spaced-apart relation along the member and an insulating material axially interposed between the electrodes, each electrode being in circuit communication with a respective portion of a source of electrical energy;

the discrete electrodes being configured to establish a first electromagnetic field in vivo between selected electrodes sufficient to cause an electromigration of a molecule relative to a target tissue and a second electromagnetic field sufficient to cause transient permeability of a cell membrane within the target tissue.

2. The device recited in claim 1, wherein the second field is higher than the first field.

3. The device recited in claim 1, wherein the member comprises:

an elongated core electrode comprising a conductive material;

a nonconductive insulator sleeve positioned in surrounding relation to a portion of the core electrode; and an outer electrode positioned in surrounding relation to a portion of the sleeve, a bottom portion of the sleeve protruding therefrom.

4. The device recited in claim 3, wherein the sleeve has a bottom portion adapted to protrude beneath a bottom of the outer electrode.

5. The device recited in claim 1, wherein the at least one member comprises a plurality of members disposed about the support in spaced relation from each other and configured to surround a periphery of at least a portion of the target tissue.

6. The device recited in claim 1, wherein the at least one member comprises a pair of members disposed in spaced-apart relation and adapted to provide at least one pair of opposite-polarity voltages approximately simultaneously on at least one electrode on each member.

7. The device recited in claim 1, further comprising means for selectively activating a selected plurality of electrodes in a predetermined pattern.

8. The device recited in claim 1, wherein the member has a portal therein for distributing a molecule therethrough, the portal adjacent at least one of the electrodes.

9. The device recited in claim 1, wherein the member comprises an elongated nonconductive post and each electrode comprises a band wrapped at least partially circumferentially about the post, each electrode in spaced relation from an adjacent electrode.

10. The device recited in claim 9, wherein the post comprises a plurality of posts affixed in spaced-apart relation to the support for surrounding at least a portion of a target tissue.

11. The device recited in claim 10, further comprising means for activating a pair of electrodes on different posts for providing an electromagnetic pulse across at least a portion of the target tissue.

12. The device recited in claim 11, wherein the activating means comprises means for activating successive pairs of electrodes in a preselected pattern.

13. A device for manipulating a molecule in vivo relative to a target tissue comprising:

a support and at least one member affixed to and extending away from the support, the member having at least two discrete, individually activatable electrodes, each electrode being in circuit communication with a respective portion of a source of electrical energy, wherein the member comprises:
  an elongated core electrode comprising a conductive material;
  a first nonconductive insulator sleeve positioned in surrounding relation to a portion of the core electrode;
  a first outer electrode positioned in surrounding relation to a portion of the sleeve, a bottom portion of the sleeve protruding therefrom;
  a second insulator sleeve positioned in surrounding relation to a portion of the first outer electrode, a bottom portion of the first outer electrode protruding therefrom; and
  a second outer electrode positioned in surrounding relation to a portion of the second sleeve;

the discrete electrodes being configured to establish a first electromagnetic field in vivo between selected electrodes sufficient to cause an electromigration of a molecule relative to a target tissue and a second electromagnetic field sufficient to cause transient permeability of a cell membrane within the target tissue.

14. The device recited in claim 13, wherein the first sleeve has a bottom portion positioned to protrude beneath a bottom of the first outer electrode and the second sleeve has a bottom portion adapted to protrude beneath a bottom of the second outer electrode.

15. A system for manipulating a molecule in vivo relative to a target tissue comprising:

a support and at least two elongated members affixed to and extending away from the support, a first member having at least one electrode and a second member having at least two discrete, individually activatable electrodes disposed in axial spaced-apart relation from each other and an insulating material interposed therebetween, each electrode being in independent circuit communication with a respective portion of a source of electrical energy;

the discrete electrodes being configured to establish a first electromagnetic field in vivo between selected electrodes sufficient to manipulate a molecule in three-dimensional space relative to a target tissue and a second electromagnetic field sufficient to cause transient permeability of a cell membrane within the target tissue.

16. The system recited in claim 15, further comprising means for activating each electrode in a preselected pattern for optimizing entry of the molecule into the target tissue.

17. A method for achieving an improved distribution and delivery of a desired molecule from an initial body location into a target tissue comprising the steps of:

inserting at least two elongated members into a body generally adjacent a target tissue, each elongated member having at least two discrete, individually activatable electrodes, each electrode being in circuit communication with a respective portion of a source of electrical energy;

establishing a first electrical potential between a pair of electrodes sufficient to cause electromigration of the desired molecule from the initial location to a location in the target tissue; and establishing a second electrical potential between a pair of electrodes higher than the first electrical potential sufficient to cause electroporation in the target tissue for enhancing a movement of the desired molecule into a cell thereof.

18. The method recited in claim 17, wherein the elongated member inserting step comprises inserting a plurality of elongated members, and the establishing steps comprise establishing a first and a second electrical potential between a first electrode on a first elongated member and a second electrode on a second elongated member.

19. The method recited in claim 18, wherein the establishing steps comprise establishing a series of first and second electrical potentials in a predetermined sequence of pulses.

20. The method recited in claim 18, wherein the plurality of members are configured to generally surround a periphery of the target tissue.

21. The method recited in claim 17, wherein the member has a lumen therein and a portal communicating therewith adapted to deliver the molecule from the lumen to the body location.

22. The method recited in claim 17, further comprising the step, following the second establishing potential step, of establishing a third electrical potential between a pair of electrodes sufficient to cause electromigration of the desired molecule within the target tissue.

23. The method recited in claim 22, wherein the establishing steps comprise establishing a series of first, second, and third electrical potentials in a predetermined sequence of pulses.

24. A method for delivering a bioactive molecule from an initial body location to a target tissue comprising the steps of:
- inserting at least two members into a body generally adjacent or into a target tissue, each member bearing at least two discrete, individually activatable electrodes, each electrode being in circuit communication with a respective portion of a source of electrical energy;
- activating a pair of electrodes to achieve an electromigration of the bioactive molecule from the initial location to a second location adjacent the target tissue; and
- activating a pair of electrodes to achieve electroporation of a cell membrane within the target tissue sufficient to permit entry of the bioactive molecule from the second location into the cell interior.

25. A method for bringing two reactive molecules into apposition at a desired target tissue site for permitting a reaction therebetween, a first molecule at a first area adjacent a target tissue site and a second molecule different from the first molecule at a second area adjacent the target tissue site, the method comprising the steps of:
- causing an electromigration of the first and the second molecule to a third area adjacent the target tissue site; and
- permitting the first and the second molecule to react at the third area.

26. The method recited in claim 25, wherein the electromigration causing step comprises the steps of:
- inserting at least one elongated member into a body generally adjacent the target tissue, each elongated member having at least two discrete electrodes, each electrode in circuit communication with and differentially activatable by a source of electrical energy; and
- establishing an electrical potential between a pair of electrodes sufficient to cause electromigration of the first and the second molecule in a desired direction toward the third area.

27. A method for making a molecule electromanipulator comprising the steps of:
- affixing at least two elongated posts to extend away from a support;
- affixing at least two discrete electrodes to each post in axially spaced-apart relation, each electrode differentially activatable;
- providing circuit communication between each electrode and a source of electrical energy, the electrodes configured to establish a low-level electromagnetic field in vivo between selected electrodes for manipulating a molecule relative to a target tissue and a higher-level electromagnetic field for causing transient permeability of a cell membrane within the target tissue; and
- providing switching means between each electrode and the electrical energy source to permit differential activation of each electrode.

28. The method recited in claim 27, further comprising means for controlling the switching means adapted to activate the electrodes in a preselected pattern.

* * * * *